United States Patent
Zhou et al.

(10) Patent No.: US 10,894,070 B2
(45) Date of Patent: Jan. 19, 2021

(54) DRUG COMPOUND FOR THE CONTROL OF BLOOD GLUCOSE, BLOOD LIPIDS AND WEIGHT

(76) Inventors: James Zhou, Beijing (CN); Dong Chen, Guangxi (CN)

( * ) Notice: Subject to any disclaimer, the term of this patent is extended or adjusted under 35 U.S.C. 154(b) by 604 days.

(21) Appl. No.: 14/008,598

(22) PCT Filed: Mar. 26, 2012

(86) PCT No.: PCT/CN2012/073042
§ 371 (c)(1),
(2), (4) Date: Jan. 16, 2014

(87) PCT Pub. No.: WO2012/130122
PCT Pub. Date: Oct. 4, 2012

(65) Prior Publication Data
US 2014/0127334 A1    May 8, 2014

(30) Foreign Application Priority Data
Apr. 1, 2011 (CN) .......................... 2011 1 0081434

(51) Int. Cl.
A61K 36/484 (2006.01)
A61K 36/815 (2006.01)
A21D 2/36 (2006.01)
A21D 2/34 (2006.01)

(52) U.S. Cl.
CPC ............ *A61K 36/484* (2013.01); *A21D 2/34* (2013.01); *A21D 2/36* (2013.01); *A61K 36/815* (2013.01)

(58) Field of Classification Search
CPC .......................... A61K 36/484; A61K 36/815
See application file for complete search history.

(56) References Cited

U.S. PATENT DOCUMENTS

| 2013/0014939 A1 | 6/2013 | Chen |
| 2013/0149393 A1 | 6/2013 | Zhou et al. |

FOREIGN PATENT DOCUMENTS

| CN | 1297754 A | * | 6/2001 | |
| CN | 1 343 728 | | 4/2002 | |
| CN | 1 423 969 | | 6/2003 | |
| CN | 1907064 A | | 2/2007 | |
| CN | 101543593 A | * | 9/2009 | |
| DE | 202008011721 U1 | * | 12/2008 | ........... A61K 36/062 |
| EP | 1 287 828 | | 3/2003 | |
| EP | 1287828 A1 | | 3/2003 | |
| EP | 1 440 688 | | 7/2004 | |
| EP | 1440688 A1 | | 7/2004 | |
| JP | 10-194959 | | 7/1998 | |
| KR | 20040040100 A | * | 5/2004 | |
| KR | 20070118754 A | | 12/2007 | |
| KR | 102007118754 | | 12/2007 | |
| WO | 2009/097238 | | 8/2009 | |
| WO | 2009097238 A1 | | 8/2009 | |
| WO | 2010/025621 | | 3/2010 | |
| WO | 2010025621 A1 | | 3/2010 | |
| WO | 2011095095 | | 8/2011 | |

OTHER PUBLICATIONS

German Patent Apln No. 112012001540.1 office action dated Dec. 5, 2014.
Fumiki Aoki et al., "Suppression by Licorice Flavonoids of Abdominal Fat Accumulation and Body Weight Gain in High-Fat Diet-Induced Obese C57BL/6J Mice", Biosci. Biotech. Biochem., vol. 71, No. 1, pp. 206-214, published in 2007.
Hiroshi Kamisoyama et al., "Investigation of the Anti-Obesity Action of Licorice Flavonoid Oil in Diet-Induced Obese Rats", Biosci. Biotech. Biochem., vol. 72, No. 12, pp. 3225-3231, published in 2008.
Kaku Nakagawa et al., "Licorice Flavonoids Suppress Abdominal Fat Accumulation and Increase in Blood Glucose Level in Obese Diabetic KK-Ay Mice", Biol. Pharm. Bull., vol. 27, No. 11, pp. 1775-1778, published in 2004.
Japanese Office action for Application No. 2014-501424 dated Oct. 27, 2015.
Examination report for Application No. GB1318936.0 dated May 31, 2017.

* cited by examiner

*Primary Examiner* — Amy L Clark

(74) *Attorney, Agent, or Firm* — Bachman & LaPointe, PC

(57) ABSTRACT

A pharmaceutical composition includes an alcohol-soluble, water insoluble, extract of *Radix Glycyrrhizae*; and wolfberry. A weight ration of the extract and wolfberry is 0.01~5:15~25. The composition is useful for controlling blood glucose and blood lipids, and for weight control. Health food products containing the recited combination are also provided.

12 Claims, No Drawings

DRUG COMPOUND FOR THE CONTROL OF BLOOD GLUCOSE, BLOOD LIPIDS AND WEIGHT

TECHNOLOGY FIELD

This invention belongs to the medicine and health food field. Specifically, this invention involves drug compound and health food compound, consisting of water-insoluble alcohol-soluble extract of *Radix Glycyrrhizae* and *Lycium Chinese*, used to control blood sugar, blood lipids and body weight, etc. Furthermore, there is no side effect with the long-term use.

TECHNOLOGY BACKGROUND

Wolfberry, also known as fruit of the Chinese wolfberry or Goji Berry, produced in Tianjin, Henan, Hebei, Shanxi, Ningxia, etc., is the fruit of solanaceae *Lycium deciduous* shrub. Wolfberry contains 14 kinds of amino acids, as well as betaine, zeaxanthine, physalin and other components, with such effect as delaying senescence. However, the property of wolfberry is sweet and warm, and its warm efficacy is especially strong, so it is not suitable for people with unrecovered internal heat, high blood pressure, colds, fever, body inflammation or diarrhea. Healthy people taking higher dose for long term are also prone to heat disease, reflected in the clinical symptom of easy sweating and hair loss in serious condition.

*Radix Glycyrrhizae's* property is sweet, and the raw *Radix Glycyrrhizae's* property is mild. It can repair the insufficiency of lienogastric, remove the heart-fire, and have the efficacies of anti-tussive, anti-inflammation and tonifying Qi. However, *Radix Glycyrrhizae* contains licorice acids compound, and has an effect similar to glucocorticoid. Long-term use will cause imbalance of sodium and potassium ions in the cell, and thus resulting in elevated blood sugar and blood pressure, so people with hypertension, hyperglycemia, obesity, kidney and heart disease and irregular menstruation shall use it with caution.

Therefore, in respect of the traditional Chinese medicine, there is no program with the collocation of only wolfberry and *Radix Glycyrrhizae* to treat disease or for health care, especially the guide for long-term use in large doses. For example, the Chinese Patent No. 00112777 describes wolfberry, licorice, ginseng and other dozens of crude drug are made into medicines in collocation, used for the prevention and treatment of hyperlipidemia, hyperglycemia and other diseases. The medicine reduces the actual amount of Chinese wolfberry and licorice, but the formula is complicated, and a lot of raw materials and product quality is difficult to control, so it is not easy to get a stabilizing and exact efficacy. Chinese Patent No. 00135732 describes more than 10 kinds of ingredients such as wolfberry, licorice and lotus leaves are made into health-care liquid, and then mixed into grape wine to become medicated wine with the efficacies of regulating blood lipids, blood pressure, and blood sugar as well as the efficacy of reducing weight. However, this medicine is not only difficult to control the quality of many raw materials and products, and not easy to get a stabilizing and exact effect, which is similar with the previous one, but also has a more narrow scope of applicable crowd due to its medicated wine form.

Other relevant current technologies published also have the above-mentioned drawbacks. For example, the health-care liquid recorded in Chinese Patent No. 02125698 not only has too many raw materials, but also needs microbial fermentation preparation, which increases the difficulty in the control of product quality stability; the major ingredient of the health foods recorded in Chinese Patent No. 02155649 is garlic, while the contents of wolfberry and *Radix Glycyrrhizae* are very low, and garlic products is not suitable for long-term large doses; the major ingredients of the health tea recorded in China Patent 200610121779 are not wolfberry and *Radix Glycyrrhizae* but *gynostemma pentaphylla* and *Linearstripe Rabdosia* Herb.

Hyperglycemia, hyperlipidemia and obesity are "rich man's disease" caused by the modern living habits. There is no permanent control method for these diseases, and the patients need long-term medication for controllability treatment. Therefore, wolfberry can't become long-term high-dose medication for these diseases due to the limitation of its side effect (where safety is a primary consideration). And there is also no health product with accurate curative effect that can be used for long-term large doses.

INVENTION SUMMARY

After the long and arduous research and with some luck, the inventor surprisingly found out that the water-insoluble alcohol-soluble extract of *Radix Glycyrrhizae* can be in collocation with wolfberry to achieve a collaborative effect and significantly improve the control effectiveness of blood glucose, blood lipids and body weight. More unexpected is that the compound can be taken in long-term large doses without side effects. Furthermore, the preparation process of collocation of wolfberry and *Radix Glycyrrhizae* is relatively simple, easy to control the product quality.

The water-insoluble alcohol-soluble extract of *Radix Glycyrrhizae* is conducive to the crumbling of wolfberry, which facilitates the preparation process. The prepared products have a longer preservation duration and shelf-life.

This invention aims to provide new compound, which can be used as drug and health food, for the control of blood sugar, blood lipids and body weight. In addition, this invention also provides the preparation method, pharmaceutical formulation or health food, as well as therapeutic applications involving the compound.

Specifically, in the first aspect, this invention provides compound containing licorice extract, consisting of alcohol-soluble and water-insoluble licorices extracts and wolfberry. The above-mentioned compound can be a pharmaceutical compound and also can be a health food compound.

In the preferred compound in the first aspect of this invention, the weight ratio of said licorice extract and wolfberry is 0.01~5:15~25, the preferred is 0.05~1:17~23, the more preferred is 0.08~0.5:19~21, and the most preferred is 0.1~0.4:20.

In the preferred compound in the first aspect of this invention, the compound is composed by alcohol-soluble and water-insoluble licorices extracts powder and wolfberry powder. Preferably, the particle size of said powder is no greater than 40 meshes, preferably no more than 50 meshes, and more preferably no greater than 60 meshes, for example, no greater than 80 meshes.

In the preferred compound in the first aspect of this invention, the said licorice extract is prepared by the extracting methods with the following steps:

(1) Immerse the licorices in water and smash them, and then reserve the solid part.

(2) Extract the solid part acquired in step (1) with alcohol, retain the extracting solution, and then dried the solid part.

In the preferred compound in the first aspect of this invention, the long-term use of the said compound is safe. In the preferred compound in the first aspect of this invention, the said compound has a longer shelf life than wolfberry powder.

In the second aspect, this invention provides a preparation method of the preferred compound in the first aspect of this invention, including first mixing the said licorice extract with wolfberry and then pulverizing them.

In the third aspect, this invention provides an product, which is a pharmaceutical formulation, comprising the first aspect compound of this invention and pharmaceutically acceptable excipients; furthermore, this invention also provides an product, which is a health food, comprising the first aspect compound of this invention and food acceptable excipients.

In the preferred product in the third aspect of this invention, the said product is capsules, water pill or cake.

The preferred product in the third aspect of this invention is in the form of a unit formulation. In the more preferred product, the unit dose of the preferred compound in the first aspect of this invention is 1 to 40 g. The preferred one is 5 to 35 g, the more preferred is 10 to 25 g, and the further more preferred is 15 to 23 g such as 19, 20 or 21 g.

In the fourth aspect, this invention provides the application of the compound of the first aspect of this invention in the prepared product, and the product is used for the prevention and/or treatment of hyperglycemia, hyperlipidemia and/or obesity. Wherein the product can be a pharmaceutical preparation and also can be a health food. The preferred product refers to the third aspect product of this invention.

The prepared product in the fourth aspect application of this invention is in the form of unit preparation, and the unit volume of the more preferred prepared product refers to the volume that can be taken in a long term.

In the fifth aspect, this invention provides a method for the prevention and/or treatment of hyperglycemia, hyperlipidemia and/or obesity, including giving the first aspect compound of this invention and the third aspect product of this invention to those in need.

INVENTION DETAILS

In the first aspect, this invention provides compound containing licorice extract, consisting of alcohol-soluble and water-insoluble licorices extracts and wolfberry. The compound of this invention is used to control blood glucose, lipids and body weight, in particular, can be safely used for long-term control of blood glucose, lipids and body weight. It can be used as a drug or pharmaceutically active material, and can also be used as a health food or health food ingredients. The compound of this invention can be a pharmaceutical compound and also can be a health food compound.

In this paper, if there is no indication to the contrary, the wolfberry refers to the fruit of *Solanaceae Lycium* wolfberry shrub. The wolfberry available in the market is usually dry wolfberry. In this invention, the preferred wolfberry is dried wolfberry, the moisture content of the more preferred wolfberry is 5~20% (w/w), and the water content of the further more preferred wolfberry is 10 to 15% (w/w). By means such as drying in the oven, the technical personnel of this field can dry the commercially available wolfberry with a high moisture content to be the wolfberry meeting the above moisture requirements.

In this paper, if there is no instruction to the contrary, the licorice refers to the whole *Radix Glycyrrhizae*, and the licorice extract refers to the extract of the whole *Radix Glycyrrhizae*. The preferred *Radix Glycyrrhizae* refers to *Glycyrrhiza uralensis, Glycyrrhiza inflata* or other licorice, or the mixtures of two or more of them. The licorice extract of this invention is compound alcohol-soluble and water-insoluble licorices extracts. The licorices extracts can be obtained by extraction with alcohol after immersion of the licorice in water. More specifically, the preparation methods of licorices extracts includes the following steps:

(1) Immerse the licorices in water and smash them, and then reserve the solid part.

(2) Extract the solid part acquired in step (1) with alcohol, retain the extract, and then dried the solid part.

Wherein, the soaking can be once or several times, such as twice. In the specific execution mode of this invention, the soaking is once. Weight ratio of licorice and water in each soaking shall be below 1:5, the more preferred is less than 1:6, the further more preferred is 1:7~12, and the most preferred weight ratio is 1:8~10.

The preferred water temperature of soaking is from 50 to 90° C., and the more preferred is 60-70° C. such as 65° C. The immersion time can be 5 to 10 hours, the more preferred is 6 to 8 hours, and the most preferred is 7 hours.

After the soaking (discarded the water), the preferred method is to wash the licorice with water again, i.e. soaking in water for a short time, such as 3 to 30 minutes. And the preferred time is 5 to 15 minutes. Then the licorice can be washed with water once or several times, the preferred is 2-5 times, and the most preferred is 3 times. Wherein, the preferred water temperature in each washing is from 50 to 70° C., and the more preferred is 55-65° C. and the most preferred is 60° C.

The preferred alcohol is ethanol, methanol, propanol, or mixtures of two or more of them; the more preferred is ≥95% (V/V) of ethanol or methanol, such as 95% (V/V) ethanol. Alcohol extraction is usually conducted with the method of water bath refluxing, such as water bath refluxing of 80~90° C., and the preferred is 85° C. water bath refluxing. Alcohol extraction can be once or several times, such as twice. The extracting solution shall be retained each time, and be merged finally. In each extraction, calculated by the used amount of the initial licorice material, the weight volume ratio of liquorice and alcohol is 1:1 to 10 (g/ml), the preferred is 1:2 to 5, and the more preferred is 1:2.5.

The mixing of licorice extract of this invention with wolfberry only in a small amount can bring lots of advantages, including synergistic increase of efficacy and health effects in the control of blood glucose, blood lipids and weight, long-term safe use and the improvement of production properties of the compound such as facilitating the production and increasing the shelf life. In the preferred compound in the first aspect of this invention, the weight ratio of said licorice extract and wolfberry is 0.01~5:15~25, the preferred is 0.05~1:17~23, the more preferred is 0.08~0.5:19~21, and the most preferred is 0.1~0.4:20.

In the preferred compound in the first aspect of this invention, the said compound is composed of alcohol-soluble and water-insoluble licorices extracts powder and wolfberry powder. Preferably, the particle size of said powder is no greater than 40 meshes, preferably no more than 50 meshes, and more preferably no greater than 60 meshes, such as no greater than 80 meshes. This can be achieved by making powder pass through the corresponding mesh sieve after crashing.

In the preferred compound in the first aspect of this invention, the long-term use of the said compound is safe. In this paper, the long-term means the time for a month or more, the preferred is two months or more such as three months. In the specific execution mode of this invention, a three-month safe use is proved to be available. In this paper, safety means, in addition to the compliance with the safety requirements of the drug or food prescribed by the State Food and Drug Administration, there is no side effect caused by long-term use of wolfberry such as easy sweating and hair loss.

In the preferred compound in the first aspect of this invention, the said compound has a longer shelf life than wolfberry powder. The shelf life can be assessed by the conventional high-humidity stability testes. For example, we can observe whether the compound of this invention will agglomerate and the time required for agglomeration under the room temperature environment with the relative humidity reaching 75%. According to the specific execution mode of this invention, the compound of this invention can have a longer shelf life such as 6 months or even longer than the wolfberry powder.

In the second aspect, this invention provides a preparation method of the preferred compound in the first aspect of this invention, including mixing the said licorice extract with wolfberry in the first place and then pulverizing them.

In addition, the optimization method of the second aspect of this invention includes the preprocessing step of wolfberry and/or extraction step of licorice. Wherein the preprocessing step of the wolfberry includes the steps drying the wolfberry (especially the commercially available wolfberry), such as drying the wolfberry to a level with the moisture content of 5~20% (w/w); the preferred moisture content is 10~15% (w/w). The licorice extraction steps include: (1) immerse the licorices in water and smash them, and then reserve the solid part; (2) extract the solid part acquired in step (1) with alcohol, retain the extracting solution, and then dried the solid part.

The optimization methods of the second aspect of this invention also include the sieving step after the crumbling. The preferred is 40 to 80 mesh sieves, such as 40-mesh, 50-mesh, 60-mesh, 70-mesh or 80-mesh sieve.

In the third aspect, this invention provides a product, which is a pharmaceutical formulation, including the first aspect compound of this invention and pharmaceutically acceptable excipients;

Furthermore, this invention also provides a product, which is a health food, comprising the first aspect compound of this invention and food acceptable excipients.

In this paper, the term "pharmaceutically acceptable excipient" comprises the pharmaceutically acceptable carrier, excipient, diluent, etc which are compatible with the pharmaceutically active ingredient. Using pharmaceutically acceptable excipients to prepare the pharmaceutical formulation is well known to the ordinary technical personnel. The pharmaceutical formulation of this invention contains the first aspect compound of this invention as the active ingredient, and it combines the compound with the pharmaceutically acceptable adjuvants (such as carrier, excipient, diluent, etc well known to ordinary technical personnel in this field) to be formulated into various preparations. The preferred is solid preparations and liquid preparations, such as tablets, pills, capsules (including sustained release or delayed-release form), powders, suspensions, granules, tinctures, syrups, emulsions, suspension liquid, injections, and other formulations, as well as a variety of sustained release dosage-forms, and thus be suitable for various administration forms, such as oral administration, parenteral injection, mucous membranes, muscles, intravenous, subcutaneous, intraocular, intradermal, or through the skin and other administration forms, in which the most preferred is oral administration. Particularly preferred excipients include dispersing agents, such as nano, nano starch dextrin nano, nano-SiO2, nano-CaCO3, nano-TiO2, zinc oxide, nano indium nano-silver, nano-aluminum hydroxide, iron oxide, nano ferric chloride, nano carbon nano-selenium, nano-alumina, and nano-magnesium oxide. Other suitable excipients include polyethylene glycols and water-soluble carrier of poly-dimensional ketones, such as PEG2000-20000 or PVP K15-K90 or PVA or PVP-PVA or CPD etc.

In this paper, the term "Acceptable Excipients in Food" include acceptable carriers, excipients, diluents, flavoring agents, coloring agents, flavoring agents on food, which are compatible with health active ingredient of food. The first aspect of composition of this invention can be added directly to food or food ingredient, for example, it can be coated on the surface of the cake or make cake after mixed with flour.

In the preferred product in the third aspect of this invention, the said product is capsules, water pill or cake.

The preferred product in the third aspect of this invention is in the form of unit preparation, Such as a tablet, pills, a pill, a capsules and a cake. The content of active constituent in unit formulation (the first aspect of composition of the compound), i.e. the unit dosage is 1~40 g, the preferred is 5~35 g, the more preferred is 10~25 g and the most preferred is 15~23 g, such as 19, 20 or 21 g. The Wolfberry powder of such unit dose is not suitable for long-term use, for it will cause side effects including sweating and hair loss, but the preparation of this invention is suitable for long-term and safely use in such unit dosage.

The preferred product in the third aspect of this invention may further include other drugs or health active ingredients for the prevention and/or treatment of hyperglycemia, hyperlipidemia and/or obesity.

In the fourth aspect, this invention provides the application of the compound in the preparation of products of the first aspect of this invention, which is used for the prevention and/or treatment of hyperglycemia, hyperlipidemia and/or obesity. The above-mentioned products can be a pharmaceutical preparation and or health food.

In this paper, the treatment can be controlled treatment i.e. the complete cure of the disease is not required, but it can prevent corresponding diseases from deteriorating or contribute to the improvement of corresponding diseases, such as lower blood sugar, reduce blood fat and/or lose weight in the process of taking products of this invention or within a limited time after withdrawal of products of this invention.

In preferred application of the fourth aspect of this invention, the described product is the product of the third aspect of this invention. Wherein the described product is in the form of unit preparation, for example the unit dose is 1 to 40 g, the preferred is 5~35 g, the more preferred is 10~25 g and the most preferred is 15~23 g, such as 19, 20 or 21 g. The formulation of this invention can be taken in such a unit dose for long-term safely; therefore the preparation product shall also include preparation specification, which recorded the above-mentioned unit dosage.

The unit volume of the more preferred prepared product for the prepared product of the preferred fourth aspect application of this invention refers to the volume that can be taken in a long term. The volume of unit preparation of product, i.e. unit volume is the volume suitable for long-term use. For example, the unit volume may be 30 or more, which can meet the taking requirements for a month or more; may be preferably 60 or more, such as 90. In addition to the proof of suitable for long-term safe taking of this invention, the long quality guarantee period proved in this invention is also the technical basis for the implementation of the technical solution with the unit volume above. Unit preparations containing the above unit volume are usually packaged in the same container (such as medicine bottle), which constitute the product (e.g. drug).

In the fifth aspect, this invention provides the method for prevention and/or treatment of hyperglycemia, hyperlipidemia and/or obesity, which includes long-term giving the composition of the first aspect of this invention or the third aspect of this invention product to people in need. People in need refer to people who need to prevent and/or treat high hyperglycemia, hyperlipidemia and/or obese people; while they usually take orally.

Wherein, the long-term refers to 1 month or more, preferably 3 months or more, such as 3 months.

Wherein, the given volume preferably of composition of the first aspect or the product of the third aspect of this invention is the effective volume for prevention and/or treatment. For example, the composition of the first aspect of this invention, the daily effective volume may be 1~40 g, the preferred is 5~35 g, the more preferred is 10~25 g and the most preferred is 15~23 g, such as 19, 20 or 21 g.

The beneficial effect of this invention is that *Radix Glycyrrhizae* extract and wolfberry can collaborate to increase the curative effect or health care effect of control of blood sugar, blood lipids or body weight or health effects, with advantages of outstanding effect, suitable for long-term safe taking, long quality guarantee period and easy production.

This invention quoted the publicly available literatures so as to describe this invention more clearly, and their full-text contents are incorporated herein as if their full text has been repeated in this paper.

For easy understanding, the following part will describe this invention with specific embodiments. It must be specially pointed out that these descriptions are demonstrative only and do not constitute a restriction on the scope of this invention. Other technical plans of this invention can be obtained by the method described in embodiments. According to the description of this instruction, many changes of this invention are obvious for technicians of its field.

Specific Implementation Methods

Plant raw materials and chemical reagents used in specific embodiments are all conventional materials bought from the market.

Embodiment 1 Preparation of Experimental Medicines (1) Preparation of Licorice Extract G018

Soak 100 g of comminuted Ural licorice herb (can be purchased from Beijing TRT, Beijing, China) into 800 ml water of 65° C.; seven hours later, filter the solution, throw away the liquid and retain the solid; wash the solid with water of 60° C. for three times respectively, and each time use 800 ml water to soak the solid for 10 min and then filter the solution and throw away the liquid. Put the washed licorice into a 60° C. drying oven for 17 hours. Add 250 ml 95% (V/V) ethanol into the solid after drying, put the container into 85° C. water for circumfluence bath for 1.5 hours, then filter the solution and retain the liquid; add 250 ml 95% (V/V) ethanol into the filtered residue, put the container into 85° C. water for circumfluence bath for 1.5 hours, then filter the solution and retain the liquid; mix two parts of filtered liquid, dry it under 60° C. for 20 hours, 3.9 g licorice extract will be obtained, named G018.

(2) Preparation of CK-Wolfberry Powder (Contrast)

Take 20 g wolfberry (can be purchased from Beijing TRT, Beijing, China), dry under 60° C. until the water content is among 12~13% (w/w), comminute them by FW135 type comminutor (purchased from Tianjin Taisite Instrument Co., LTD), the comminutor's rotational speed is 24000 r/min and the comminution time is 30 s. Wolfberry powder can not pass through a 100 mesh sieve, if it is a 80 mesh sieve, we find that about 80% of wolfberry powder can not pass through the sieve, this might because that the content of polysaccharide in wolfberry is relatively high, then it is not easy to comminute, thus the production is affected. Therefore, use a 60 mesh sieve, about 90% of wolfberry powder can pass through, and the particle diameter of CK-wolfberry powder obtained by this way is no more than 60 meshes.

Conduct the stability test at the room temperature of 22 to 28° C., and the relative humidity of 75%, it's found that CK-wolfberry powder will be caked within 12 hours, indicating that CK-wolfberry powder is hard to store and guarantee its quality.

(3) Preparation of 0.5-G018 Wolfberry Powder

Refer to the method in (2) mentioned above, take 20 g wolfberry, dry them and mix them with 0.1 g G018, then comminute them by FW135 type comminutor, the comminutor's rotational speed is 24000 r/min and the comminution time is 30 s. use a 80 mesh sieve, we find that about 50% of the mixed powder can not pass through, although it is can be seen that adding G018 is conducive to the comminution of wolfberry, the trapped amount of mixed powder still can not be ignored, so we use a 60 mesh sieve, then more than 95% of wolfberry powder can pass through, and the particle diameter of wolfberry powder obtained by this way is not more than 60 mesh.

Conduct the stability test at the room temperature of 22 to 28° C., and the relative humidity of 75%, it's found out that 0.5-G018 wolfberry powder will not be caked within 24 hours, so it is much easier to store and guarantee quality compared to CK-wolfberry powder.

(4) Preparation of 2-G018 Wolfberry Powder

Refer to the method in (2) mentioned above, take 20 g wolfberry, dry them and mix them with 0.4 g G018, then comminute them by FW135 type comminutor with the rotational speed of 24,000 r/min and comminution time of 30 s. Filter the mixed powder by a 80-mesh sieve (only less than 5% of the mixed powder can not pass through), and the particle diameter of 2-G018 wolfberry powder obtained by this way is no more than 80 meshes.

Conduct the stability test at the room temperature of 22 to 28° C., and the relative humidity of 75%, it's found out that 2-G018 wolfberry powder will not be caked within 72 hours, so it has the advantage of being much easier to store and guarantee quality compared to CK-wolfberry powder, and under the condition of sealed package, its quality guarantee period is expected to be 6 months longer than that of CK-wolfberry powder with the same package.

(5) Preparation of Formulations

The above CK-wolfberry powder, 0.5-G018 wolfberry powder and 2-G018 wolfberry powder can be directly put into capsules to make capsule formulation respectively, and they can also be made into water pill formulation by water pill machine, and they can also be made into the shape of cake.

Embodiment 2 Clinical Observation on the Short-Term Efficacy of All Drugs in Embodiment 1 on Postprandial Blood Glucose Controlling for High-Blood-Glucose Patient The postprandial blood glucose of Type 2 diabetics insensitive to insulin is an important index of abnormal glucose metabolism, so the effect of drugs in reducing blood glucose can be inspected through the examination on postprandial blood glucose of diabetics in this embodiment. Implement according to the clinical experiment standard issued by the State Food and Drug Administration, people after random grouping (45-56 years old, three in one group, fasting blood glucose is above 7.5 mM/L and postprandial blood glucose is above 10 mM/L) take orally CK-wolfberry powder, 0.5-G018 wolfberry powder, 2-G018 wolfberry powder and ordinary food (soybean) respectively prepared in Embodiment 1, and the dose they intake is metered by the above powder or soybean, all are 20 g. 30 min after taking the medicine before the meal in the morning, test the blood glucose two hours after patients eat 300 g boiled corn and the results are shown in Table I.

The results show that CK-wolfberry powder, 0.5-G018 wolfberry powder and 2-G018 wolfberry powder all play a significant role in the control of postprandial blood glucose of diabetics with high blood sugar, and its efficacy works immediately, which is obviously better than the efficacy of ordinary food (soybean), among them the effect of 0.5-G018 wolfberry powder and 2-G018 wolfberry powder is better than that of CK-wolfberry powder alone.

der and ordinary food (soybean) respectively prepared in Embodiment 1, and the dose they intake is metered by the above powder or soybean, all are 20 g, and take the medicine or ordinary food once a day before breakfast for four weeks. Four weeks later, draw blood and assay the blood glucose, blood fat and body weight, and the results are shown in the following Table II.

The results show that although ordinary food (soybean) plays little role in lowering cholesterol, it has no effect of blood glucose reduction or losing weight; using CK-wolfberry powder alone results in the blood glucose reduction of less than 10%, blood fat reduction of less than 3% and weight reduction of 2 Kg, which is completely worse than using 2-G018 wolfberry powder; 2-G018 wolfberry powder achieves an average blood glucose reduction of about 29.1%, average serum cholesterol reduction of about 46.6% and average weight reduction of 5.3 Kg. In addition to the difference in efficacy, it is even more remarkable that three months later after taking 20 g of CK-wolfberry powder every day, the patient become prone to sweating, and even one patient suffers the side effect of hair loss; in contrast, take 20 g of 2-G018 wolfberry powder every day, one week

TABLE I

Blood glucose comparison before/after meal with/without drug intake

| Drug | Patient No. | Gender | Age | Without drug intake, before/after meal | | Drug intake before/after meal | |
|---|---|---|---|---|---|---|---|
| | | | | Blood glucose (mM/L) | Blood glucose (mM/L) | Blood glucose (mM/L) | Blood glucose (mM/L) |
| 2-G018 wolfberry powder | 11-01 | F | 53 | 8.1 | 12.3 | 7.9 | 6.5 |
| | 11-02 | M | 56 | 7.5 | 11.6 | 7.6 | 5.6 |
| | 11-04 | M | 54 | 7.9 | 12.6 | 7.7 | 6.8 |
| | Average | | | 7.8 | 12.2 | 7.7 | 6.3 |
| | Ratio of glucose reduction | | | | | | 48% |
| 0.5-G018 wolfberry powder | 11-05 | F | 56 | 7.8 | 10.9 | 7.6 | 5.9 |
| | 11-06 | M | 50 | 9.1 | 12.8 | 9.4 | 6.3 |
| | 11-07 | F | 53 | 7.6 | 11.5 | 7.8 | 7.0 |
| | Average | | | 8.2 | 11.7 | 8.6 | 6.4 |
| | Ratio of glucose reduction | | | | | | 45% |
| CK-wolfberry powder | 11-08 | F | 53 | 7.5 | 12.9 | 7.6 | 8.5 |
| | 11-09 | M | 55 | 7.9 | 11.8 | 7.9 | 8.9 |
| | 11-10 | F | 51 | 7.6 | 12.5 | 8.3 | 8.5 |
| | Average | | | 7.7 | 12.4 | 7.9 | 8.6 |
| | Ratio of glucose reduction | | | | | | 31% |
| Soybean | 11-11 | F | 48 | 7.8 | 12.5 | 7.5 | 11.6 |
| | 11-12 | M | 53 | 8.4 | 11.9 | 8.3 | 10.8 |
| | 11-13 | F | 55 | 8.1 | 12.5 | 8.5 | 12.6 |
| | Average | | | 8.1 | 12.3 | 8.1 | 11.7 |
| | Ratio of glucose reduction | | | | | | 5% |

Embodiment 3 Clinical Observation on the Long-Term Efficacy of All Drugs in Embodiment 1 on Blood Fat, Blood Glucose and Body Weight Implement according to the clinical experiment standard issued by State Food and Drug Administration, patients after random grouping (45-59 years old, three in one group, men and women of equal number, fasting blood glucose is above 7.5 mM/L and serum cholesterol is above 300 mg/100 ml) take orally CK-wolfberry powder, 2-G018 wolfberry powlater, the patients' appetite decreases but their physical strength increases, which is beneficial for patients with high cholesterol and high blood sugar and is not a side effect, without such side effect as easy sweating and hair loss.

TABLE II

Fasting blood glucose, blood fat and body weight comparison before and after long-term drug intake

| | | | | Before take medicine | | | After take medicine | | |
|---|---|---|---|---|---|---|---|---|---|
| | Patient No. | Gender | Age | Blood glucose (mM/L) | Body weight (Kg) | Cholesterol (mg/100 ml) | Blood glucose (mM/L) | Body weight (Kg) | Cholesterol (mg/100 ml) |
| CK-wolfberry pill | 06-11 | M | 53 | 8.6 | 69 | 315 | 8.0 | 66 | 310 |
| | 06-12 | M | 51 | 7.8 | 73 | 328 | 7.5 | 71 | 318 |
| | 06-13 | M | 55 | 9.0 | 71 | 361 | 8.3 | 69 | 349 |
| | Average | | | 8.5 | 71 | 334 | 7.9 | 69 | 326 |
| | Reduction | | | | | | 7.1% | 2 | 2.9% |
| 2-G018 Wolfberry pill | 06-14 | M | 57 | 9.1 | 75 | 286 | 6.1 | 69 | 201 |
| | 06-15 | M | 49 | 7.4 | 68 | 363 | 5.9 | 63 | 196 |
| | 06-16 | F | 55 | 9.3 | 76 | 429 | 6.3 | 71 | 179 |
| | Average | | | 8.6 | 73 | 359.3 | 6.1 | 68 | 192 |
| | Reduction | | | | | | 29.1 | 5.3 | 46.6% |
| Soybean powder | 11-11 | F | 48 | 7.8 | 79 | 12.5 | 8.0 | 81 | 11.6 |
| | 11-12 | M | 53 | 8.4 | 66 | 11.9 | 8.8 | 69 | 10.8 |
| | 11-13 | F | 55 | 8.1 | 74 | 12.5 | 8.5 | 75 | 12.6 |
| | Average | | | 8.1 | 73 | 12.3 | 8.4 | 75 | 11.7 |
| | Reduction | | | | | | -4% | -2 | 5% |

The invention claimed is:

1. A pharmaceutical composition comprising a combination consisting of: (a) an alcohol-soluble, water-insoluble extract of *Radix Glycyrrhizae*; and (b) wolfberry, wherein (a) and (b) are present in the combination in a weight ratio of (a):(b) of 0.1-0.4:20, respectively, wherein the composition is in the form of a capsule, pill, tablet or emulsion.

2. The composition of claim 1, wherein the extract is an alcohol-soluble and water-insoluble licorice extract powder and the wolfberry is a wolfberry powder.

3. The composition of claim 1, wherein the *Radix Glycyrrhizae* extract is prepared by: (i) immersing a licorice starting material in water and smashing the licorice starting material to provide a solid part; (ii) reserving the solid part;
(iii) extracting the solid part obtained in step (ii) with alcohol to provide an alcohol soluble extract; and (iv) retaining the alcohol soluble extract.

4. The composition of claim 1, wherein a unit dose of the composition contains 1-40 g of the combination per capsule, pill, tablet or emulsion.

5. The composition of claim 1, wherein the composition is incorporated into a pharmaceutical preparation or health food for treating hyperglycemia, hyperlipidemia and/or obesity.

6. The composition of claim 2, wherein the licorice extract powder and the wolfberry powder have a particle size of no greater than 40 mesh.

7. The composition of claim 2, wherein the licorice extract powder and the wolfberry powder have a particle size of no greater than 50 mesh.

8. The composition of claim 2, wherein the licorice extract powder and the wolfberry powder have a particle size of no greater than 60 mesh.

9. The composition of claim 2, wherein the licorice extract powder and the wolfberry powder have a particle size of no greater than 80 mesh.

10. The composition of claim 4, wherein the unit dose contains 5-35 g of the combination.

11. The composition of claim 4, wherein the unit dose contains 10-25 g of the combination.

12. The composition of claim 4, wherein the unit dose contains 15-23 g of the combination.

* * * * *